United States Patent
Ivancev et al.

(10) Patent No.: US 9,724,187 B2
(45) Date of Patent: *Aug. 8, 2017

(54) PARAPLEGIA PREVENTION STENT GRAFT

(71) Applicant: Cook Medical Technologies LLC, Bloomington, IN (US)

(72) Inventors: Krasnodar Ivancev, London (GB); Blayne A. Roeder, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 176 days.

This patent is subject to a terminal disclaimer.

(21) Appl. No.: 14/701,011

(22) Filed: Apr. 30, 2015

(65) Prior Publication Data
US 2015/0230916 A1   Aug. 20, 2015

Related U.S. Application Data

(63) Continuation of application No. 13/707,323, filed on Dec. 6, 2012, now Pat. No. 9,095,456, which is a
(Continued)

(51) Int. Cl.
*A61F 2/07* (2013.01)
*A61F 2/89* (2013.01)

(52) U.S. Cl.
CPC .................. *A61F 2/07* (2013.01); *A61F 2/89* (2013.01); *A61F 2250/0039* (2013.01)

(58) Field of Classification Search
CPC .... A61F 2/07; A61F 2/82; A61F 2/856; A61F 2/86; A61F 2/89; A61F 2002/061; A61F 2002/072; A61F 2250/0039
See application file for complete search history.

(56) References Cited

U.S. PATENT DOCUMENTS 5,387,235 A   2/1995   Chuter
5,425,765 A   6/1995   Tiefenbrun et al.
(Continued)

FOREIGN PATENT DOCUMENTS

WO   WO 99/11198 A1   3/1999
WO   WO 00/25847      5/2000
(Continued)

OTHER PUBLICATIONS

Patent Examination Report No. 1 for corresponding Australian Application No. 20100306961, dated Mar. 14, 2013 (4 pages).
(Continued)

*Primary Examiner* — Ryan J Severson
(74) *Attorney, Agent, or Firm* — Brinks Gilson & Lione

(57) ABSTRACT

A stent graft for deployment into the aorta of a patient has a tubular body with a proximal portion of a selected diameter; preferably a reduced diameter portion, distal of the proximal portion, having a diameter less than the selected diameter; a tapered portion, extending between the proximal portion and the reduced diameter portion; and optionally a distal portion, distal of the reduced diameter portion. At least three, preferably four or five, low profile side arms are provided, preferably in the reduced diameter portion and/or the tapered portion, for connection of an arm extension to an aortic branch vessel. All but one of the side arms are to be connected at the physician's choice, depending on the anatomy of the patient. One side arm is to provide temporary profusion to external of the stent graft after deployment of the stent grant into the aorta, and is subsequently blocked.

20 Claims, 3 Drawing Sheets

Related U.S. Application Data continuation-in-part of application No. 13/502,001, filed on May 16, 2012, now Pat. No. 9,034,027, which is a continuation-in-part of application No. 13/457,092, filed on Apr. 26, 2012, now Pat. No. 9,149,382, and application No. 13/502,001, filed as application No. PCT/US2010/052446 on Oct. 13, 2010.

(60) Provisional application No. 61/581,475, filed on Dec. 29, 2011, provisional application No. 61/526,061, filed on Aug. 22, 2011, provisional application No. 61/480,091, filed on Apr. 28, 2011, provisional application No. 61/278,814, filed on Oct. 13, 2009.

(56) References Cited

U.S. PATENT DOCUMENTS

| | | |
|---|---|---|
| 5,445,600 A | 8/1995 | Abdulla |
| 5,609,627 A | 3/1997 | Goicoechea et al. |
| 5,628,783 A | 5/1997 | Quiachon et al. |
| 5,676,696 A | 10/1997 | Marcade |
| 5,676,697 A | 10/1997 | McDonald |
| 5,720,776 A | 2/1998 | Chuter et al. |
| 5,746,766 A | 5/1998 | Edoga |
| 5,776,142 A | 7/1998 | Gunderson |
| 5,824,055 A | 10/1998 | Spiridigliozzi et al. |
| 5,948,017 A | 9/1999 | Taheri |
| 5,984,955 A | 11/1999 | Wisselink |
| 6,019,788 A | 2/2000 | Butters et al. |
| 6,099,548 A | 8/2000 | Taheri |
| 6,106,549 A | 8/2000 | Taheri |
| 6,143,002 A | 11/2000 | Vietmeier |
| 6,187,033 B1 | 2/2001 | Schmitt et al. |
| 6,206,931 B1 | 3/2001 | Cook et al. |
| 6,210,429 B1 | 4/2001 | Vardi et al. |
| 6,287,315 B1 | 9/2001 | Wijeratne et al. |
| 6,478,813 B1 | 11/2002 | Keith et al. |
| 6,478,817 B2 | 11/2002 | Schmitt et al. |
| 6,524,335 B1 | 2/2003 | Hartley et al. |
| 6,576,009 B2 | 6/2003 | Ryan et al. |
| 6,645,242 B1 | 11/2003 | Quinn |
| 6,663,666 B1 | 12/2003 | Quiachon et al. |
| 6,695,875 B2 | 2/2004 | Stelter et al. |
| 6,723,116 B2 | 4/2004 | Taheri |
| 6,793,672 B2 | 9/2004 | Khosravi et al. |
| 6,827,726 B2 | 12/2004 | Parodi |
| 6,849,087 B1 | 2/2005 | Chuter |
| 6,852,116 B2 | 2/2005 | Leonhardt et al. |
| 6,918,925 B2 | 7/2005 | Tehrani |
| 6,939,370 B2 | 9/2005 | Hartley et al. |
| 6,974,471 B2 | 12/2005 | Van Schie et al. |
| 7,014,653 B2 | 3/2006 | Ouriel et al. |
| 7,144,421 B2 | 12/2006 | Carpenter et al. |
| 7,169,176 B2 | 1/2007 | Lauterjung |
| 7,232,459 B2 | 6/2007 | Greenberg et al. |
| 7,235,095 B2 | 6/2007 | Haverkost et al. |
| 7,238,198 B2 | 7/2007 | Hartley et al. |
| 7,294,147 B2 | 11/2007 | Hartley |
| 7,306,623 B2 | 12/2007 | Watson |
| 7,407,509 B2 | 8/2008 | Greenberg et al. |
| 7,435,253 B1 | 10/2008 | Hartley et al. |
| 7,445,610 B2 | 11/2008 | Adams et al. |
| 7,537,606 B2 | 5/2009 | Hartley et al. |
| 7,645,298 B2 | 1/2010 | Hartley et al. |
| 7,699,883 B2 | 4/2010 | Douglas |
| 7,771,462 B1 | 8/2010 | Davidson et al. |
| 7,806,917 B2 | 10/2010 | Xiao |
| 7,828,837 B2 | 11/2010 | Khoury |
| 7,862,604 B1 | 1/2011 | Marcade et al. |
| 7,914,572 B2 | 3/2011 | Hartley et al. |
| 7,927,367 B2 | 4/2011 | Chuter |
| 9,034,027 B2 * | 5/2015 | Ivancev ............... A61F 2/07 623/1.13 |
| 9,095,456 B2 * | 8/2015 | Ivancev ............... A61F 2/82 |
| 9,149,382 B2 * | 10/2015 | Greenberg ............ A61F 2/07 |
| 2001/0012962 A1 * | 8/2001 | Schmitt ................ A61F 2/06 623/1.31 |
| 2001/0049534 A1 * | 12/2001 | Lachat ................ A61F 2/954 606/108 |
| 2003/0199967 A1 | 10/2003 | Hartley et al. |
| 2004/0098079 A1 | 5/2004 | Hartley et al. |
| 2004/0106972 A1 | 6/2004 | Deaton |
| 2004/0106978 A1 | 6/2004 | Greenberg et al. |
| 2004/0215327 A1 | 10/2004 | Doig et al. |
| 2005/0102018 A1 | 5/2005 | Carpenter et al. |
| 2005/0102021 A1 | 5/2005 | Osborne |
| 2005/0131518 A1 | 6/2005 | Hartley et al. |
| 2005/0149166 A1 | 7/2005 | Schaeffer et al. |
| 2005/0171597 A1 | 8/2005 | Boatman et al. |
| 2005/0171598 A1 | 8/2005 | Schaeffer |
| 2005/0182476 A1 | 8/2005 | Hartley et al. |
| 2005/0222668 A1 | 10/2005 | Schaeffer et al. |
| 2005/0222669 A1 | 10/2005 | Purdy |
| 2005/0222672 A1 | 10/2005 | Shmulewitz |
| 2005/0273155 A1 | 12/2005 | Bahler et al. |
| 2006/0058864 A1 | 3/2006 | Schaeffer et al. |
| 2006/0089704 A1 | 4/2006 | Douglas |
| 2006/0184228 A1 | 8/2006 | Khoury |
| 2006/0229707 A1 | 10/2006 | Khoury |
| 2007/0083215 A1 | 4/2007 | Hamer et al. |
| 2007/0219614 A1 | 9/2007 | Hartley |
| 2007/0219621 A1 | 9/2007 | Hartley et al. |
| 2007/0233220 A1 | 10/2007 | Greenan |
| 2007/0244547 A1 | 10/2007 | Greenan |
| 2007/0250154 A1 | 10/2007 | Greenberg et al. |
| 2007/0299499 A1 | 12/2007 | Hartley et al. |
| 2008/0255581 A1 | 10/2008 | Bourang et al. |
| 2009/0030502 A1 | 1/2009 | Sun et al. |
| 2009/0048663 A1 | 2/2009 | Greenberg |
| 2009/0099648 A1 | 4/2009 | Yu |
| 2009/0125098 A1 | 5/2009 | Chuter |
| 2009/0171438 A1 | 7/2009 | Chuter et al. |
| 2009/0182405 A1 | 7/2009 | Arnault de la Menardiere et al. |
| 2010/0023110 A1 | 1/2010 | Schaeffer |
| 2010/0063576 A1 | 3/2010 | Schaeffer et al. |
| 2010/0249899 A1 | 9/2010 | Chuter et al. |
| 2010/0268327 A1 | 10/2010 | Bruszewski et al. |
| 2011/0054594 A1 | 3/2011 | Mayberry et al. |
| 2012/0041535 A1 | 2/2012 | Huser et al. |
| 2012/0290069 A1 * | 11/2012 | Ivancev ............... A61F 2/07 623/1.13 |
| 2012/0323303 A1 | 12/2012 | Ivancev |
| 2013/0046371 A1 | 2/2013 | Greenberg et al. |
| 2013/0138199 A1 * | 5/2013 | Ivancev ............... A61F 2/82 623/1.11 |

FOREIGN PATENT DOCUMENTS

| | | |
|---|---|---|
| WO | WO 2004/002365 A1 | 1/2004 |
| WO | WO 2004/002370 A1 | 1/2004 |
| WO | WO 2004/017867 A1 | 3/2004 |
| WO | WO 2004/017868 A1 | 3/2004 |
| WO | WO 2004/028399 A2 | 4/2004 |
| WO | WO 2005/034808 A1 | 4/2005 |
| WO | WO 2005/034810 A1 | 4/2005 |
| WO | WO 2008/007397 A1 | 1/2008 |
| WO | WO 2010/127040 A1 | 11/2010 |
| WO | WO 2011/047004 A1 | 4/2011 |
| WO | WO 2011/116308 A1 | 9/2011 |

OTHER PUBLICATIONS

Partial European Search Report, dated Dec. 14, 2012, European Patent Application No. 12164809.1, European Patent Office, The Netherlands (6 pages).

Communication pursuant to Article 94(c) EPC, dated Mar. 11, 2015 for corresponding European Patent Application No. 12164809.1 (7 pages).

Extended European Search Report, dated Apr. 16, 2013 for corresponding European Patent Application No. 12164809.1 (14 pages).

International Search Report and Written Opinion of the Interna-

(56) References Cited

OTHER PUBLICATIONS tional Searching Authority for corresponding PCT/US2010/052446, mailed Jan. 17, 2011 (13 pages).
Extended European Search Report, dated Mar. 5, 2014 for European Patent Application No. 13275292.4 (5 pages).
Examination Report, dated Oct. 14, 2015 for European Patent Application No. 13275292.4 (4 pages).
Extended European Search Report, dated May 13, 2016 for European Patent Application No. 16152812, 8 pages.

* cited by examiner

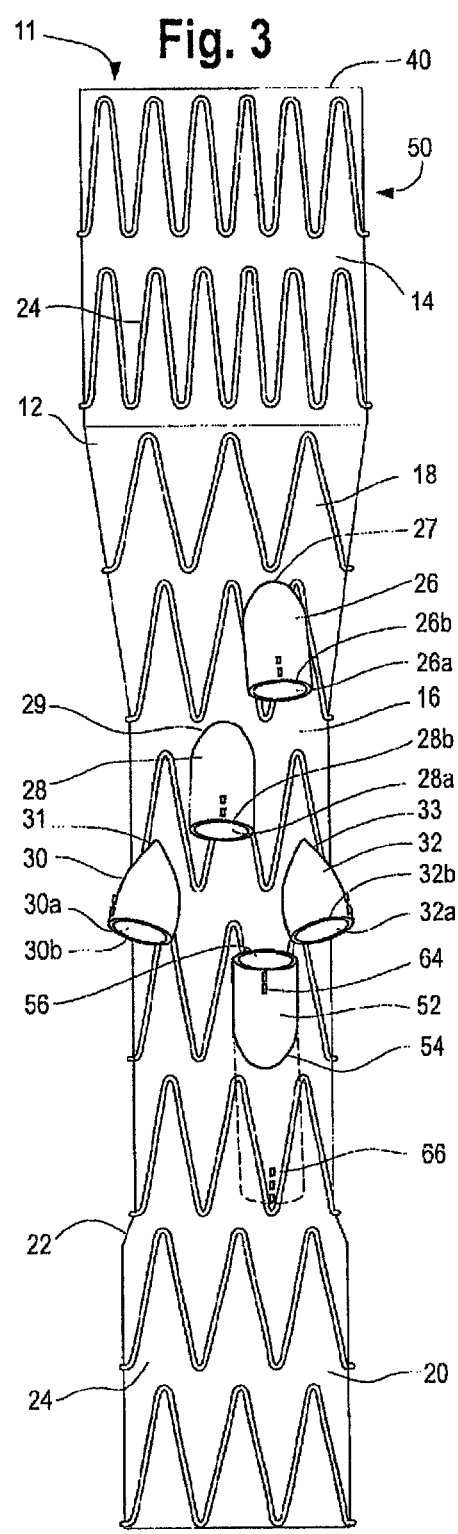
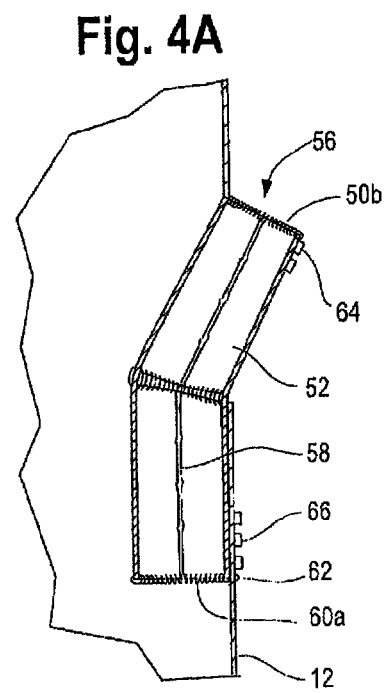
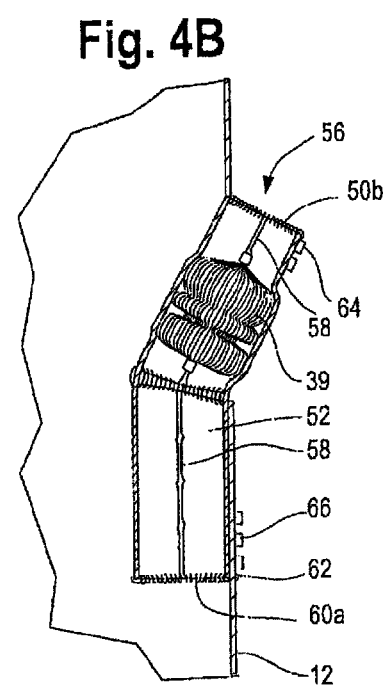

PARAPLEGIA PREVENTION STENT GRAFT

RELATED APPLICATIONS

This application is a continuation of U.S. patent application Ser. No. 13/707,323, filed Dec. 6, 2012, which is a continuation-in-part of U.S. patent application Ser. No. 13/502,001, filed May 16, 2012, which is a 35 USC 371 application from PCT Application No. PCT/US2010/052446, filed Oct. 13, 2010; and claims priority to U.S. Provisional Application No. 61/278,814, filed Oct. 13, 2009; and is also a continuation-in-part of U.S. patent application Ser. No. 13/457,092, filed Apr. 26, 2012, and claims the benefit of U.S. Provisional Application No. 61/581,475, filed Dec. 29, 2011, and U.S. Provisional Application No. 61/526,061, filed Aug. 22, 2011, and U.S. Provisional Applications No. 61/480,091, filed Apr. 28, 2011. All of the foregoing applications are hereby incorporated by reference in their entirety.

FIELD OF INVENTION

This invention relates to a medical device and more particularly to an implantable endovascular device, such as a stent graft for deployment in the aorta of a patient.

BACKGROUND

This invention will be discussed in general with respect to aortic aneurysms and the use of an implantable device such as a stent graft to bridge an aneurysm and in particular in the descending aorta, but the invention is not so limited and may be used for any region of the human or animal body and any type of implantable device.

An aortic aneurysm can be abdominal (occurring in the abdomen) or thoracoabdominal (a single aneurysm occurring partially in the thorax and partially in the abdomen). Abdominal aortic aneurysms are sometimes referred to as "AAA"; while thoracoabdominal aortic aneurysms are sometimes referred to as "TAAA". A stent graft can be used to bridge an aortic aneurysm, but where there are side branch arteries from the aorta it may be desirable to have side branches extending from the stent graft to give a blood supply to as many side branch arteries as possible.

After an endovascular operation to place a stent graft into the descending aorta, the human or animal body can in time adapt to lack of blood supply from some arteries which are excluded by the stent graft. For instance, blood supply via the intercostal arteries to the spinal cord can be alternatively achieved via other arteries, such as for instance the celiac artery, the superior mesenteric artery, lumbar and internal iliac arteries.

There can be a problem, however, of blood supply immediately after an operation, at least in part relating to blood pressure. Furthermore, patients with thoracoabdominal aortic aneurysms may have upward-facing renal arteries. It may be difficult to cannulate an upward-facing renal artery, as tracking a stiff bridging stent out of the branch and into the artery may pull the wire out of the branch.

BRIEF SUMMARY

The invention provides, in one embodiment, an implantable device such as a stent graft for deployment into the aorta of a patient, the device comprising a tubular body of a biocompatible graft material, the tubular body defining a main lumen therethrough, and at least three (preferably at least four or five) low profile side arms in the tubular body, each low profile side arm comprising a respective side arm lumen therethrough and the main lumen being in fluid communication with the respective side arm lumens; wherein at least two (preferably at least three or four) of the low profile side arms point downwardly and open externally of the tubular body to allow the flow of blood in a distal direction, and at least one of the low profile side arms points upwardly and opens externally of the tubular body to allow the flow of blood in a proximal direction.

The tubular body may comprise (a) a proximal portion of a selected diameter; (b) a reduced diameter portion, distal of the proximal portion, having a diameter which is less than the selected diameter; and (c) a tapered portion, extending between the proximal portion and the reduced diameter portion. The tubular body may further comprise (d) a distal portion, distal of the reduced diameter portion, having a diameter which is more than that of the reduced diameter portion. The main lumen is in fluid communication with the respective side arm lumens, and the side arms can each be connected to an arm extension, which arm extensions can each be connected to an aortic branch vessel. At least two, preferably three or four, of the low profile side arms point downwardly and open externally to allow the flow of blood in a distal direction, and at least one of the low profile side arms points upwardly and opens externally to allow the flow of blood in a proximal direction. At least one of the low profile side arms (downwardly-pointing, upwardly-pointing, or both) is optionally allowed to provide perfusion to external of the tubular body after deployment and is subsequently blocked.

The invention also provides, in one embodiment, a process of deploying a stent graft into the aorta of a patient, the patient having a celiac artery, a superior mesenteric artery, a right renal artery and a left renal artery, and the stent graft being as described above, and having at least five low profile side arms, at least four of which point downwardly; the process comprising (a) selecting, from among the at least five low profile side arms, four low profile side arms to be connected to four arm extensions, the arm extensions to be connected to the celiac artery, the superior mesenteric artery, the right renal artery and/or the left renal artery, depending on the orientation of these arteries in the patient; (b) so connecting the low profile side arms and arm extensions; (c) allowing at least one of the remaining low profile side arms (which is not selected to be connected to an arm extension to be connected to an artery) to provide perfusion to external of the tubular body after deployment; and (d) subsequently blocking the low profile side arms which are allowed to provide perfusion to external of the tubular body.

The one or more branches left open in this embodiment are allowed for a time to perfuse the aneurysm to reduce the chances of paraplegia, and are subsequently blocked. A preferred location of an upward facing branch is slightly more anterior and facing slightly to the left, to make targeting an upward-facing renal artery more workable.

The invention also provides, in another embodiment, a process of deploying a stent graft into the aorta of a patient, the patient having a celiac artery, a superior mesenteric artery, a right renal artery and a left renal artery, and the stent graft being as described above and having four low profile side arms, at least one of which points upwardly; wherein the process comprises two medical procedures; wherein the first medical procedure comprises selecting, from among the four low profile side arms, three low profile side arms to be connected to three arm extensions, the three arm extensions to be connected to three of the celiac artery, the superior mesenteric artery, the right renal artery and the left renal artery, depending in part on the orientation of these arteries in the patient, and so connecting the three selected low profile side arms and arm extensions; and wherein the low profile side arm which is not selected to be connected in the first procedure to an arm extension to be connected to an artery, is allowed to provide perfusion to external of the tubular body after deployment; and wherein the second medical procedure comprises subsequently connecting the low profile side arm which was not connected in the first procedure to an arm extension to be connected to an artery, to the artery not connected in the first procedure. The artery not connected in the first medical procedure, but connected in the second medical procedure, can be the celiac artery, the superior mesenteric artery, the right renal artery, or the left renal artery. The right renal artery and the left renal artery can be connected to arm extensions which are connected (a) to two low profile side arms which point downwardly, (b) to one low profile side arm which points downwardly and to one low profile side arm which points upwardly, or (c) to two low profile side arms which point upwardly (if two upwardly pointing arms are available).

In a preferred embodiment, the implantable device is deployed into the descending aorta and the plurality of low profile side arms comprises four low profile side arms which are connected to the celiac artery, superior mesenteric artery, the right renal artery and the left renal artery.

The stent graft may also have a paraplegia prevention vent tube in fluid communication with the main lumen and open externally in a proximal direction to external of the tubular body in the region defined by the reduced diameter portion or the tapered portion, wherein the paraplegia prevention vent tube provides temporary perfusion externally in a proximal direction to external of the stent graft after deployment of the stent graft into the aorta; and is subsequently blocked. The paraplegia prevention vent tube is open internally, preferably in a distal direction.

The preferred application for the implantable device of the invention is for deployment into the aorta of a patient to bridge an aneurysm and to be connected to the celiac artery, the superior mesenteric artery, the right renal artery and the left renal artery. However, one or two of these arteries may not be diseased, and accordingly may be left connected to the aorta, in which case as few as three low profile side arms may be needed. Likewise, if the device is used in a region of the body other than in the aorta of a patient, as few as three low profile side arms may be needed.

BRIEF DESCRIPTION OF THE DRAWINGS

To assist with understanding the invention, reference will now be made to the accompanying drawings. In the drawings:

FIG. 3 shows a stent graft according to an alternative embodiment of the invention;

FIG. 4A is a side view of the paraplegia prevention vent tube of FIG. 3;

FIG. 4B is a side view of the paraplegia prevention vent tube of FIG. 3 closed off with a plug;

DESCRIPTION OF PREFERRED EMBODIMENTS

Figure 1:
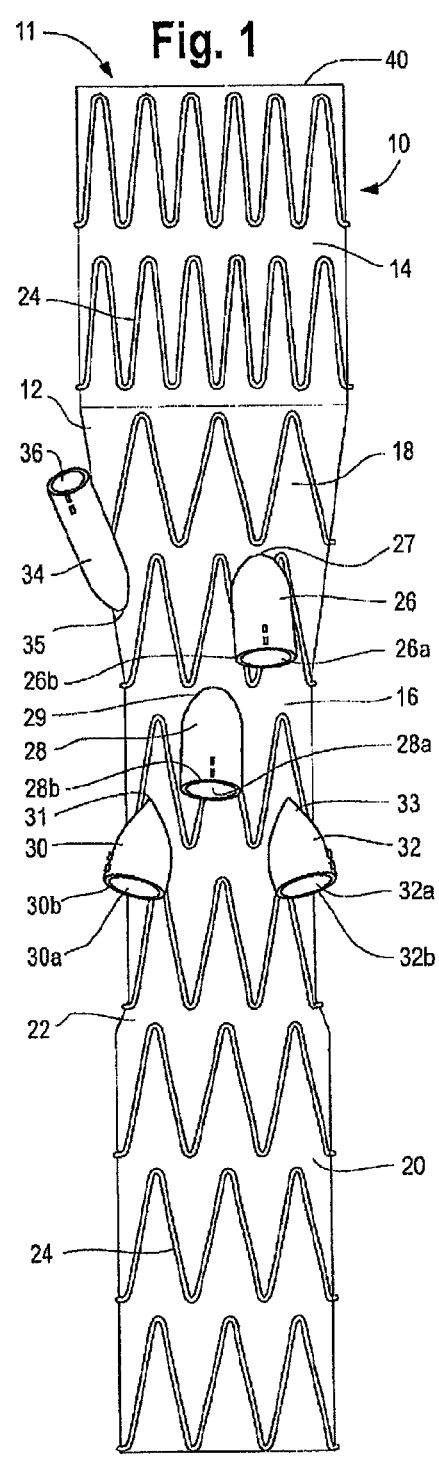
FIG. 1 shows a stent graft according to one embodiment of the invention.
Figure 2A:
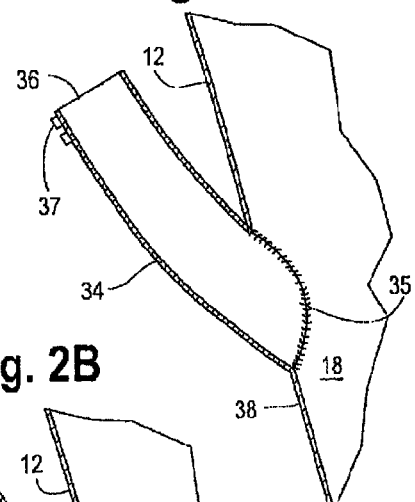
FIG. 2A is a side view of the paraplegia prevention vent tube of FIG. 1.
Figure 2B:
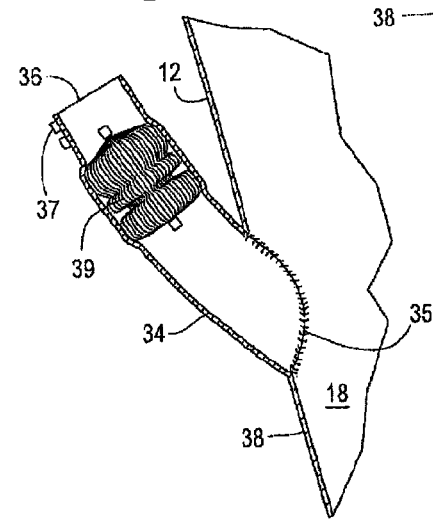
FIG. 2B is a side view of the paraplegia prevention vent tube of FIG. 1 closed off with a plug.

Now looking at the FIGS. 1, 2A and 2B of the drawings, a stent graft 10 according to one embodiment of the invention is shown that comprises a tubular body 12 of a biocompatible graft material. The tubular body 12 has a main lumen 11 therethrough. The tubular body 12 comprises a proximal portion 14 of a selected diameter and a reduced diameter portion 16, distal of the proximal portion 14, having a diameter which is less than the selected diameter. The tubular body 12 also has a proximal tapered portion 18 extending between the proximal portion 14 and the reduced diameter portion 16. The tubular body 12 may also comprise a distal portion 20, distal of the reduced diameter portion 16, which distal portion 20 has a diameter that is less than the selected diameter of the proximal portion 14, and that is greater than the diameter of the reduced diameter portion 16; and a distal tapered portion 22 extending between reduced diameter portion 16 and the distal portion 20. In this embodiment the proximal portion 14 has a diameter of approximately 34 mm; the tapered portion has a diameter of approximately 34 mm at a wide end adjacent the proximal portion, and a diameter of approximately 20 mm at a narrow end adjacent the reduced diameter portion; and the reduced diameter portion 16 has a diameter of approximately 20 mm. The distal portion 20, if present, has a diameter of approximately 24 mm.

Each of the proximal portion 14, the proximal tapered portion 18, the reduced diameter portion 16, and the distal portion 20 are supported by stents 24 affixed to the graft material by adhesive, by stitching or by another method of affixation. The stents 24 may be inside or outside of the tubular body 12. The stents 24 may take any form. In one embodiment, each of the stents 24 is preferably a self expanding Gianturco Z-stent formed from nitinol, stainless steel or other metal wire.

In the embodiments illustrated in FIGS. 1, 2A, 2B and 2C, or in FIGS. 3, 4A and 4C, four low profile side arms 26, 28, 30 and 32 are shown. The low profile side arms 26, 28, 30 and 32 extend from fenestrations (holes) 27, 29, 31 and 33 in the reduced diameter portion 16 or the proximal tapered portion 18. Each low profile side arm 26, 28, 30, 32 comprises a respective side arm lumen 26a, 28a, 30a, 32a therethrough, and the main lumen 11 is in fluid communication with the respective side arm lumens 26a, 28a, 30a, 32a. Each of the four low profile side arms 26, 28, 30 and 32 may be supported by supporting stents 58 (see FIGS. 4A and 4B), and may have reinforcing rings 60a (see FIGS. 4A and 4B) at their internal ends, and/or reinforcing rings 60b (see FIGS. 4A and 4B), 26b, 28b, 30b and 32b at their external ends.

The four low profile side arms 26, 28, 30 and 32 in these embodiments are for use to receive arm extensions for entry into the celiac artery, the superior mesenteric artery, the right renal artery and the left renal artery respectively.

As further shown in the Figures, the tubular body 12 also may include a paraplegia prevention vent tube 34 extending from a fenestration 35 in the proximal tapered portion 18 and in fluid communication with the main lumen 11. The paraplegia prevention vent tube 34 opens to external of the tubular body 12 at the open proximal end 36 of paraplegia prevention vent tube 34, in the region defined by the reduced diameter portion 16 and the distal tapered portion 22. The paraplegia prevention vent tube 34 is used to provide temporary perfusion to external of the stent graft 10 after deployment of the stent graft 10 into the aorta, and is subsequently blocked.

The paraplegia prevention vent tube 34 can be formed from a biocompatible graft material and have a diameter of approximately 6 mm and a length of from about 16 to about 32 mm.

FIG. 2A shows a side view of a paraplegia prevention vent tube 34. The vent tube 34 is connected to the wall 38 of the tubular body 12 at a fenestration 35. The tube 34 may be un-stented along its length, as shown in FIG. 2A.

The paraplegia prevention vent tube 34 preferably has radiopaque markers 37 at its proximal end to assist with later location by radiographic techniques. Radiopaque markers also may be placed at the fenestration 35, and/or along the length of tube 34.

FIG. 2B shows a side view of a paraplegia prevention vent tube 34 closed off with a plug 39. The plug 39 may be deployed endovascularly and released into the paraplegia prevention vent tube 34. The plug 39 may be an Amplatzer Vascular Plug (AGA Medical Corporation, MN, USA). Other desirable plugs include the Zenith Flex® AAA Endovascular Graft Iliac Plug available from Cook Medical Incorporated of Bloomington, Ind., USA. The plug 39 may have suitable oversizing to ensure it seals in the paraplegia prevention vent tube 34.

Figure 2C:
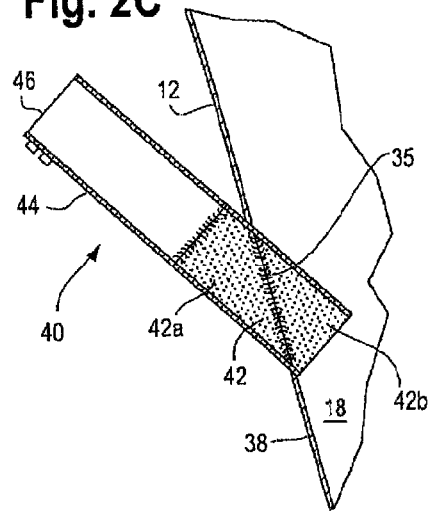
FIG. 2C is a side view of an alternative embodiment of a paraplegia prevention vent tube.

FIG. 2C shows a side view of an alternative embodiment of a paraplegia prevention vent tube 40. In this embodiment the paraplegia prevention vent tube 40 includes a low profile side arm 42 which has a portion 42a external of the wall 38 of the tubular body 12 at a fenestration 35 and a portion 42b internal of the wall 38. Connected to the low profile side arm 42 is a tubular portion 44 with an open proximal end 46. The tubular portion 44 can be stented (see supporting stents 58 in FIGS. 4A and 4B) or unstented along its length.

Referring to FIGS. 3, 4A and 4B, stent graft 50 comprises a tubular body 12 of a biocompatible graft material. The tubular body 12 has a main lumen 11 therethrough. The tubular body 12 comprises a proximal portion 14 of a selected diameter, a reduced diameter portion 16, distal of the proximal portion 14, having a diameter less than the selected diameter; and a proximal tapered portion 18 extending between the proximal portion 14 and the reduced diameter portion 16. The tubular body 12 may also comprise a distal portion 20 which has a diameter less than the selected diameter and greater than the diameter of the reduced diameter portion 16 distal of the proximal portion 14, and a distal tapered portion 22 extending between the reduced diameter portion 16 and the distal portion 20. In this embodiment the proximal portion 14 has a diameter of approximately 34 mm, the reduced diameter portion 16 has a diameter of approximately 20 mm, and the distal portion has a diameter of approximately 24 mm.

Each of the proximal portion 14, the distal portion 20 and the reduced diameter portion 16 are supported by stents 24 affixed to the graft material by adhesive, stitching or other method of affixation. The stents 24 may be inside or outside of the tubular body 12.

Four low profile side arms 26, 28, 30 and 32, are shown extending from fenestrations 27, 29, 31 and 33 in the reduced diameter portion 16 or the proximal tapered portion 18. Each low profile side arm 26, 28, 30, 32 comprises a respective side arm lumen 26a, 28a, 30a, 32a therethrough and the main lumen 11 is in fluid communication with the respective side arm lumens 26a, 28a, 30a, 32a.

The four low profile side arms 26, 28, 30 and 32 receive arm extensions (not shown in FIGS. 1, 2A, 2B, 2C, 3, 4A and 4B, see arm extension 81 in FIG. 6) for entry into the celiac artery, the superior mesenteric artery, the right renal artery and the left renal artery, respectively.

The tubular body 12 can also include a paraplegia prevention vent tube 52 extending from a fenestration 54 in the reduced diameter portion 16 and in fluid communication with the main lumen 11. The paraplegia prevention vent tube 52 opens to external of the tubular body 12 at open proximal end 56 in the region defined by the reduced diameter portion 16 and the tapered portion 22. The paraplegia prevention vent tube 52 is used to provide temporary perfusion to external of the stent graft 50 after deployment of the stent graft 50 into the aorta and is subsequently blocked.

The paraplegia prevention vent tube 52 can be formed from a biocompatible graft material and have a diameter of 6 mm and a length of from 16 to 32 mm. The paraplegia prevention vent tube 52 can comprise supporting stents 58 and reinforcing rings 60a and 60b at the internal and external ends respectively.

The paraplegia prevention vent tube 34 comprises radiopaque markers 37 at its proximal and distal ends to assist with later location by radiographic techniques. In this embodiment, there are two markers 64 in line at the proximal end and three markers 66 in line on the outside of the tubular body 12 at the distal end of the paraplegia prevention vent tube 52.

An exemplary stent graft 50 may have dimensions as follows:

| | |
|---|---|
| Overall length | 236 mm |
| Length of proximal portion | 48 mm |
| Length of proximal tapered portion | 43 mm |
| Length of reduced diameter portion | 71 mm |
| Length of distal tapered portion | 6 mm |
| Length of distal portion | 68 mm |
| Diameter of proximal portion | 34 mm |
| Diameter of tapered portion, adjacent proximal portion | 34 mm |
| Diameter of tapered portion, adjacent reduced diameter portion | 20 mm |
| Diameter of reduced diameter portion | 20 mm |
| Diameter of distal portion | 24 mm |

Taking the circumference of the stent graft 50 as a clock face with the anterior point at 12 o'clock, the side arms and paraplegia prevention vent tube may be placed, for example, as follows:

| | |
|---|---|
| celiac artery | Distance from proximal end 89 mm, 8 mm diameter, length 18 mm, position 1 o'clock |
| superior mesenteric artery | Distance from proximal end 110 mm, 8 mm diameter, length 21 mm, position 12 o'clock |
| right renal artery | Distance from proximal end 128 mm, 6 mm diameter, length 18 mm, position 10:45 o'clock |
| left renal artery | Distance from proximal end 128 mm, 6 mm diameter, length 18 mm, position 2:45 o'clock |
| paraplegia prevention vent tube | Distance from proximal end 130 mm, 6 mm diameter, length 32 mm, position 1:30 o'clock |

FIG. 4A shows a side view of a paraplegia prevention vent tube 52. The paraplegia prevention vent tube 52 is connected by stitching 62 to the wall 38 of the tubular body 12.

FIG. 4B shows a side view of a paraplegia prevention vent tube 52 closed off with a plug 39. The plug 39 is deployed endovascularly and released into the paraplegia prevention vent tube 52.

Figure 5:
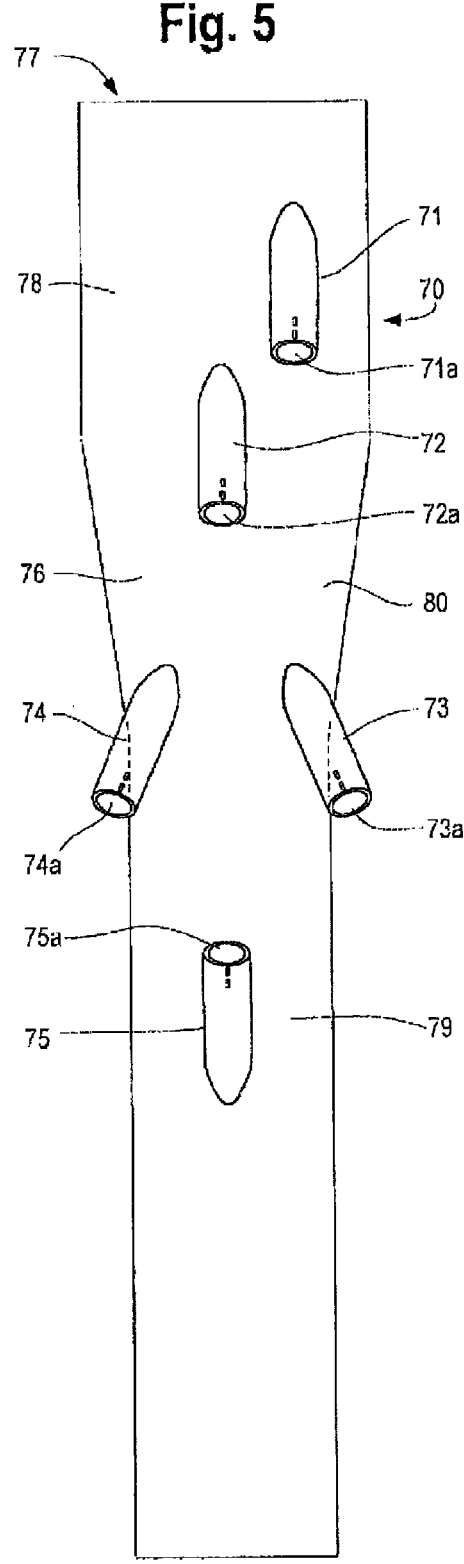
FIG. 5 shows an alternate form of the invention, which comprises a stent graft according to the invention which includes at least five low profile side arms.

FIG. 5 shows an alternate form of the invention, which comprises a stent graft 70 according to the invention, which includes at least five low profile side arms 71, 72, 73, 74, 75. Although five low profile side arms 71-75 are shown in FIG. 5, more may be used if desired; or three or four may be used.

The stent graft 70 shown in FIG. 5 comprises a tubular body 76 of a biocompatible graft material, the tubular body 76 defining a main lumen 77 therethrough. The tubular body 76 comprises a proximal portion 78 of a selected diameter, a reduced diameter portion 79, distal of the proximal portion 78, which has a diameter which is less than the selected diameter, and a tapered portion 80 extending between the proximal portion 78 and the reduced diameter portion 79. Five low profile side arms 71-75 are provided in this embodiment (although as few as three low profile side arms may be provided), each low profile side arm 71-75 comprising a respective side arm lumen 71a-75a therethrough, and the main lumen 77 being in fluid communication with the respective side arm lumens 71a-75a. The side arms 71-75 each are for connection of an arm extension to an aortic branch vessel. At least four of the low profile side arms 71-74 in this embodiment (or at least two or three low profile side arms in embodiments in which there are three of four low profile side arms altogether) point downwardly and open externally to allow the flow of blood in a distal direction. At least one of the low profile side arms 75 points upwardly and opens externally to allow the flow of blood in a proximal direction. At least one of the low profile side arms 71-75 (preferably side arms 73, 74, closer to upwardly-pointing low profile side arm 75) is optionally allowed to provide perfusion to external of the tubular body after deployment and is subsequently blocked. At least one of the downwardly-pointing low profile side arms 71-74, or at least one of the upwardly-pointing low profile side arms 75, or both, is optionally allowed to provide perfusion to external of the tubular body after deployment and is subsequently blocked.

In a non-limiting example, the stent graft 70 may be provided with four downwardly-pointing low profile side arms 71-74, and one upwardly-pointing low profile side arm 75, as shown in FIG. 5, any one of which low profile side arms can be optionally allowed to provide perfusion to external of the tubular body after deployment and be subsequently blocked. A physician deploying the stent graft 70 may select any four of the five low profile side arms 71-75, depending on the orientation of these arteries in the patient, for example low profile side arms 71, 72, 74 and 75, to be connected to the celiac artery, the superior mesenteric artery, the right renal artery and the left renal artery, respectively, and connect the low profile side arms (via intermediate arm extensions 81) in accordance with the selection. The low profile side arm (for example, side arm 73) not selected for connection to the celiac artery, the superior mesenteric artery, the right renal artery or the left renal artery can be used to provide temporary perfusion to external of the stent graft 70 (for example, through side arm lumen 73a), after deployment of the stent graft 70 into the aorta, and then subsequently be blocked.

The stent graft 70 according to this embodiment can also comprise in addition a paraplegia prevention vent tube (not shown in FIG. 5, see paraplegia prevention vent tube 34 in FIGS. 1, 2A and 2B, paraplegia prevention vent tube 40 in FIG. 1C; and paraplegia prevention vent tube 52 in FIGS. 3, 4A and 4B) in fluid communication with the main lumen 77, which opens externally in a proximal direction to external of the tubular body 76 in the region defined by the portion 79 of reduced diameter and the tapered portion 80, wherein the paraplegia prevention vent tube 34, 40, 52 provides temporary perfusion to external of the stent graft 70 after deployment of the stent graft 70 into the aorta; and wherein the paraplegia prevention vent tube is subsequently blocked.

Figure 6:
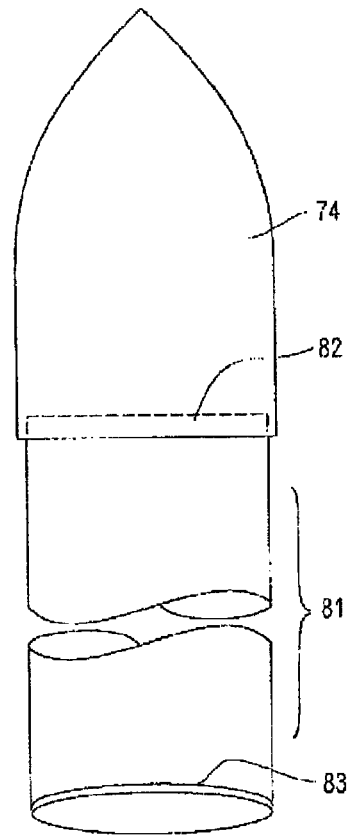
FIG. 6 shows an arm extension, and its connection to a low profile side arm.

FIG. 6 shows an arm extension 81 and its connection to a low profile side arm such as low profile side arm 74 by means such as adhesive at junction 82. Stitching or another method of affixation can alternatively be used. A reinforcing ring 83 can be placed at the end of arm extension 81.

The invention provides enhanced utility for an off-the-shelf thoracoabdominal aortic aneurysm graft, as it allows for placement of the renal branches in various configurations without user modification. The standard placement of the at-least-five-low-profile-side-arm embodiment would be with four downward-facing branches connected to the celiac artery, the superior mesenteric artery and the two renal arteries, in which case the upward-facing branch can be occluded, covered with a bifurcated component, or left open temporarily to perfuse the aneurism. Two other (non-standard) configurations of the at-least-five-low-profile-side-arm embodiment have either an upward-facing left renal artery or an upward-facing right renal artery connected to an upward-facing branch, with the unconnected downward-facing branch occluded or left open temporarily to perfuse the aneurism. Such a graft can be made available with pre-loaded catheters and/or wires, and is amenable to the use of low-profile or extra-low-profile materials, as reduction of delivery system size is not limited by preloaded sheaths. The invention therefore provides an improved entry angle for the wires and catheter in renal cannulation.

Throughout this specification the term "distal" means further away in the direction of blood flow away from the heart, and "proximal" means nearer to the heart. The flow of blood in the distal and proximal directions means flow away from the heart and towards the heart, respectively. "Left" and "right" are from the patient's perspective.

Hartley et al. U.S. Pat. No. 7,914,572 discloses various forms of low profile side arms, and the teachings therein are incorporated by reference herein in their entirety.

Throughout this specification various indications have been given as to the scope of the invention, but the invention is not limited to any one of these but may reside in two or more of these combined together. The examples are given for illustration only and not for limitation. Throughout the specification and the claims that follow, unless context requires otherwise, the words "comprise" and "include" and variations such as "comprising" and "including" will be understood to imply the inclusion of a stated integer or group of integers but not the exclusion of any other integer or group of integers.

The invention claimed is:

1. A branched prosthesis comprising:
   a tubular body of biocompatible graft material having a proximal end, a distal end, and an internal lumen;
   a proximal portion having a first diameter;
   a distal portion having a second diameter;
   an intermediate portion between the proximal portion having a third diameter less than both the first diameter and the second diameter;
   a tapered portion distal to the proximal portion and proximal to the intermediate portion;
   at least one upwardly extending arm at least partially disposed in the tapered portion and having an end open extending toward the proximal end and configured to permit fluid flow therethrough;

at least one downwardly extending side arm in the intermediate portion having an open end extending toward the distal end and configured to permit fluid flow therethrough;

wherein a portion of the at least one upwardly extending side arm is disposed within the internal lumen.

2. The prosthesis of claim 1, including a second upwardly extending arm in the tapered portion.

3. The prosthesis of claim 1, wherein the diameter of the distal portion is less than the diameter of the proximal portion.

4. The prosthesis of claim 1, wherein each of the at least one upwardly extending arm and the at least one downwardly extending arm are configured to receive an arm extension.

5. The prosthesis of claim 1, wherein the at least one upwardly extending arm has at least one radiopaque marker at its open end.

6. The prosthesis of claim 1, wherein the at least one upwardly extending side arm is circumferentially offset from at least one of the downwardly extending side arms.

7. The prosthesis of claim 1, wherein the at least one upwardly extending side arm has a length of from 16 mm to 32 mm and a diameter of 6 mm.

8. The prosthesis of claim 1, further comprising a distal tapered portion between the intermediate portion and the distal portion.

9. The prosthesis of claim 1, wherein the intermediate portion has a constant diameter and is stented along its length.

10. The prosthesis of claim 1, wherein the at least one upwardly facing side arm has a distal opening engaging a fenestration in the tapered portion.

11. The prosthesis of claim 1, further including a second downwardly extending arm in the intermediate portion.

12. A branched prosthesis comprising:
a tubular body of biocompatible graft material having a proximal end, a distal end, and an internal lumen;
a proximal portion having a first diameter;
a distal portion having a second diameter;
an intermediate portion between the proximal portion having a third diameter less than both the first diameter and the second diameter;
a tapered portion distal to the proximal portion and proximal to the intermediate portion having a variable diameter;
at least two fenestrations in the tapered portion;
at least one fenestration in the intermediate portion;
at least two upwardly extending arms each extending from a respective fenestration in the tapered portion and each having an end open extending away from its fenestration and toward the proximal end of the prosthesis;
at least one downwardly extending side arm extending from the fenestration in the intermediate portion and having an open end extending away from the fenestration and toward the distal end of the prosthesis;
wherein a portion of the at least two upwardly extending arms is disposed within the internal lumen.

13. The prosthesis of claim 12, wherein the diameter of the distal portion is less than the diameter of the proximal portion.

14. The prosthesis of claim 12, wherein each of the at least two upwardly extending arms and the at least one downwardly extending arm are configured to receive an arm extension.

15. The prosthesis of claim 12, wherein the at least two upwardly extending arms have at least one radiopaque marker at their open ends.

16. The prosthesis of claim 12, wherein the upwardly extending arms are circumferentially offset from the at least one of the downwardly extending arm.

17. The prosthesis of claim 12, wherein at least one of the at least two upwardly extending arms has a length of from 16 mm to 32 mm and a diameter of 6 mm.

18. The prosthesis of claim 12, further comprising a distal tapered portion between the intermediate portion and the distal portion.

19. The prosthesis of claim 12, wherein the intermediate portion has a constant diameter and is stented along its length.

20. The prosthesis of claim 12, where each of the open ends of the at least two upwardly extending arms and the at least one downwardly extending arm has at least one radiopaque marker.

* * * * *